United States Patent
Sotoyama et al.

(12)

(10) Patent No.: US 6,451,344 B1
(45) Date of Patent: Sep. 17, 2002

(54) SUGAR COATED TABLETS

(75) Inventors: Kazuyoshi Sotoyama; Teruhiko Mizota; Yuzo Asano; Tetsushi Mori; Yuriko Iiyama, all of Kanagawa (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 0 days.

(21) Appl. No.: 09/674,247

(22) PCT Filed: Jan. 22, 1999

(86) PCT No.: PCT/JP99/00285

§ 371 (c)(1),
(2), (4) Date: Oct. 30, 2000

(87) PCT Pub. No.: WO99/56732

PCT Pub. Date: Nov. 11, 1999

(30) Foreign Application Priority Data

Apr. 30, 1998 (JP) .......................................... 10-136009

(51) Int. Cl.$^7$ .................................................. A61K 9/36

(52) U.S. Cl. ........................................................ 424/479
(58) Field of Search ................................. 424/474, 479, 424/475, 480

(56) References Cited

FOREIGN PATENT DOCUMENTS

| JP | 55-136218 | * | 10/1980 |
| JP | 5-4926 | * | 1/1993 |
| JP | 5-186337 | * | 7/1993 |

\* cited by examiner

*Primary Examiner*—James M. Spear
(74) *Attorney, Agent, or Firm*—Oblon, Spivak, McClelland, Maier & Neustadt, P.C.

(57) ABSTRACT

This invention is a sugar coated tablet which has anticariogenic properties, containing no sucrose but a mixture of lactulose and raffinose with various physiological effects, as a sugar coat base, and these tablets comprises a core tablet and a sugar base coating the same, the sugar base contains the above mixture as the active ingredient.

12 Claims, No Drawings

SUGAR COATED TABLETS

This application is a 371 of PCT/JP 99/00285 filed Jan. 22, 1999.

1. Technical Field

The present invention relates to a sugar-coated tablet formed by coating a core tablet using a mixture of lactulose and raffinose having various physiological effects as the sugar coating base.

In this specification, the core tablet refers to a tablet that is produced by the tabletizing of a composition that exhibits pharmacological action, and the sugar coating base refers to a composition that is used to coat the core tablet.

2. Background Art

Currently, coatings for medicinal preparations are frequently used in order to mask the flavor or odor of a drug, ensure the safety of the druggist by preventing the generation of drug dust, improve the stability of the drug by protecting the drug from light, water and oxygen, and improve the efficacy or stability of the drug by imparting solubility in intestines or controlled release effects. In addition, known methods for coating medicinal preparations involve gelatin coating, dry coating, sugar coating, film coating and powder coating, but gelatin coating and dry coating are almost never used for the sole purpose of coating, whereas powder coating has been the subject of much investigation and is considered to be a future technology. Consequently, sugar coating and film coating are currently the main methods.

Conventional sugar coating bases have been aqueous solutions of sugar (syrups), and it is said that tablets with excellent hermetic properties and smooth surface are obtained by the formation of tight block-form structures of sugar crystal. Calcium lactate is also known, in addition to sugar, as a sugar coating base, and other known substances include talc used as a sugar coating dispersion agent, precipitated calcium carbonate used as a sugar coating suspension agent, gelatin, gum arabic and pullulan used as sugar coating binders, and carnauba wax used as a sugar coating glossing agent (Hisashi Ichibangase, Kaneto Uekama, and Yuki Odagiri, Eds."Drug Product Development [Iyakuhin no Kaihatsu] Vol. 12, Preparation Materials [Seizai Sozail] I" Hirokawa Shoten, Heisei 2 Nen/1990).

In addition, the use of sugar alcohols as materials for coating foodstuffs has been disclosed (Japanese Laid-Open Patent Publication No. H9-313109, 1997), and the use of fine granulated sugar and corn starch as materials for coating compound-grain granules soluble in intestines has been disclosed (Japanese Laid-Open Patent Publication No. H5-186337, 1993).

On the other hand, lactulose is a type of disaccharide composed of galactose and fructose (4-O-$\beta$-D-galactopyranosyl-$\alpha$-D-fructose), and is manufactured by subjecting lactose to the Lobry de Bruyn transformation. Lactulose is known to be a Bifidobacteria stimulating factor (Diagnosis and New Drugs [Shindan to Shinyaku], Vol. 10(5), p.75 (1973)). The substance is used in prepared powdered milk and powdered milk for weaning. In addition, lactulose is known to have the action of mitigating diseases such as hepatic encephaly and hepatic coma, and the substance has previously been used for treating these patients (Psychiatric Medicine [Seishin Igaku], Vol. 15(10), 1101 (1973)). However, when lactulose is used by itself as a sugar coating base, its high viscosity makes it impossible to uniformly coat the core tablet.

Raffinose is a type of trisaccharide that is composed of D-glucose and D-fructose, and is manufactured from a beet syrup by isolating with chromatography. Raffinose has already received a general evaluation as a foodstuff material for special health needs by the Japan Health and Nutrition Foodstuff Society [Nihon Kenkou. Eiyou Shokuhin Kyoukail]. A method for manufacturing sugar coatings has also been disclosed in which a sucrose syrup containing raffinose at an extremely low concentration of 2% (wt %, likewise below when not otherwise specified) or less is used for coating (Japanese Patent Publication No. S58-50968 (1983)).

However, as is clear from the prior art described above, sugar-coated tablets produced using a sugar coating base which contains, as its effective component, a mixture in which at least an equivalent amount of raffinose is mixed with lactulose having various physiological actions are unknown, and are absent from the literature.

SUMMARY OF THE INVENTION

The present invention provides a sugar-coated tablet that employs, as the sugar coating base, a mixture composed of raffinose and lactulose having various physiological effects, which does not employ any sucrose, and has anticariogenic properties.

The present invention relates to a sugar-coated tablet formed by coating a core tablet with a sugar coating base that contains, as its effective component, a mixture of lactulose and raffinose.

The present invention provides a sugar-coated tablet that does not stick to the oral cavity when taken, has no unpleasant texture when ingested, a good sensation (mouthfeel) and excellent taste.

DISCLOSURE OF THE INVENTION

With the foregoing in view, the inventors began with the use of lactulose having various physiological effects as a sugar coating base, attempting to manufacture a sugar-coated tablet using a sugar coating base composed of lactulose alone, and mixtures of lactulose and sucrose, oligosaccharides, sugar alcohols and other sugars. However, adequate product quality could not be obtained in the form of a sugar-coated tablet because it was not possible to uniformly coat the core tablet due to excessive viscosity.

The inventors thus carried out painstaking investigations towards a solution to these problems, and arrived at the present invention upon discovering that when at least one part (by weight) of raffinose is mixed with respect to 1 part (by weight) of lactulose for use as the sugar coating base, the viscosity of the mixed aqueous solution can be greatly reduced, making it possible to provide a sugar-coated tablet with a uniformly coated core tablet.

It is an object of the invention to provide a sugar-coated tablet formed using a sugar coating base that is a mixture of raffinose and lactulose having various physiological effects, containing no sucrose, which is primarily used in conventional sugar coating bases, which has anticariogenic properties result from the use of lactulose and raffinose.

A solution to the above problems provided by the present invention is a sugar-coated tablet formed by coating a core tablet with a sugar coating base that contains a mixture of lactulose and raffinose as its effective component.

The present invention, in a preferred aspect, contains a mixture containing a ratio of at least 1 part (by weight, likewise below when not otherwise specified) of raffinose with respect to 1 part (by weight) of lactulose.

In another preferred aspect, the core tablet contains, as its effective component, one or both of (a) and (b) below:

(a) cell powder of one or more selected from the group consisting of microorganisms of the genus Bifidobacterium, microorganisms of the genus Lactobacillus, microorganisms of the genus Streptococcus, microorganisms of the genus Pediococcus and microorganisms of the genus Leuconostoc (these microorganisms are all referred to below as "lactic acid bacteria"), and (b) one or more selected from the group consisting of lactoferrin, peptide and lactulose.

The present invention is described below.

The lactulose and raffinose used in the sugar coating base of the present invention are commercially-available products, and can be manufactured by well-known methods. For example, lactulose can be manufactured as follows based on the methods disclosed in Japanese Laid-Open Patent Publication No. H3-169888 (1991) and Japanese Laid-Open Patent Publication No. H6-228179 (1994). Sodium hydroxide is added to a 10 wt % aqueous solution of commercial lactose, and said mixture is heated for 30 min at a temperature of 70° C., and cooled. Subsequently, the cooled solution is purified with an ion exchange resin, concentrated, and cooled to bring about crystallization. The unreacted lactose is then removed to obtain a lactulose aqueous solution with a solids content of about 68% (lactulose is contained in the solids content at about 79%). This aqueous solution is then passed through a strong acid ion exchange column to remove the component containing lactulose, whereupon the substance is concentrated to obtain a purified lactulose aqueous solution with a solids content of about 68% (lactulose is contained in the solids content at about 86%). This method is described in Japanese Laid-Open Patent Publication H3-169888 (1991).

In addition, the lactulose aqueous solution (syrup) obtained by the method described above is concentrated to a solids content of about 72%, this concentrated solution is cooled to 15° C., lactulose trihydrate crystal is added as seed crystal, and the solution is gradually cooled as necessary to 5° C. over 7 days while stirring to generate crystals. After 10 days, the solid content of the supernatant is reduced to about 61%, and crystals are separated with a filter cloth centrifuge from the solution containing the crystals. The crystals are washed in cold water at 5° C., and are dried to obtain lactulose crystals with a purity of 95% or greater (Japanese Laid-Open Patent Publication H6-228179 (1994)). The lactulose that is used in the present invention is preferably as high a purity as possible, with material having a purity of 95% or greater being particularly-preferred.

The raffinose used in the sugar coating base of the present invention is a commercially-available product, which commercially available product is generally manufactured from beet syrup by the method described below. Beet syrup is subjected to chromatography in order to remove the fraction containing the raffinose, which is then concentrated and crudely crystallized. The crude crystals are then dissolved, filtered, and purified to collect crystals that are then dried to obtain the purified crystal product (Technology for the Effective Use of New Foodstuff Materials [Shokuhin Shinsozai Yuukou Riyou Gijutsu] Series No. 6 "Raffinose", p.2, Incorporated Confectionery General Technology Center (Shadanhoujin Kashi Sougou Gijutsu Senta, 1996).

In the present invention, a sugar coating base is used that has, as its effective component, a mixture of at least one part of raffinose, and preferably 1.5–10 parts, with respect to one part of lactulose manufactured as described above.

The core tablet of the sugar-coated tablet of the present invention can be any core tablet containing various types of well-known effective components for drug tablets, and is a material that is produced by tabletizing a drug composition that exhibits various effects.

Particularly desirable core tablets used in the sugar-coated tablet of the present invention are materials that contain lactic acid bacteria biomass powder. This lactic acid bacteria biomass powder can be live biomass powder or dead biomass powder, but live bacteria powders are preferred because they have intestinal regulating actions. The biomass powder of the lactic acid bacteria can be a commercially-available product, or can be prepared by well-known methods (for example, Japanese Laid-Open Patent Publication No. H1-221319 (1989). However, an example is presented below.

A seed culture of one or more types of microorganism selected from the group consisting of microorganisms of the genus Bifidobacterium, microorganisms of the genus Lactobacillus, microorganisms of the genus Streptococcus, microorganisms of the genus Pediococcus and microorganisms of the genus Leuconostoc is bulk cultured by a common method, and various sugars, amino acids, starches, gelatin, nonfat dry milk or other dispersion media having protective action are added as necessary to the bacteria that are separated from the culture solution. The material is then freeze-dried to prepare a dry biomass. A more detailed preparation method for biomass powders of lactic acid bacteria is found in Reference Examples 1 to 4 below.

The lactulose that is used in the core tablet is the same as the material used for the above sugar coating base.

Also, the lactoferrin that is used in the core tablet is a commercially-available product or a substance that is manufactured by a well-known method, for example, the method disclosed in Japanese Patent Publication No. H6-13560 (1994), and can be manufactured as described below.

CM-Sephadex C-50 (made by Pharmacia) with a volume expansion of 3.0 and a hemoglobin adsorption capacity of 3.9 g/100 mL having carboxymethyl ion exchange groups is swelled in water and used as an Na-type ion exchanger. This material is introduced into raw nonfat milk, and is stirred for 16 h at 4° C. in order to bring about contact therewith, the ion exchanger is removed, and is loaded into a column. Water is then passed through the column to remove the nonfat milk content that has attached to the ion exchanger. 1.6% sodium chloride solution is then passed through the column and the first fraction adsorbed to the ion exchanger (proteins other than lactoferrin) is released and removed. Subsequently, 5% sodium chloride solution is passed through the column, and the liquid is recovered. Sodium chloride is then removed from the recovered liquid using an ultrafiltration film (made by DDS) with a differential molecular weight of 20,000, and the resulting concentrated liquid is freeze dried to obtain lactoferrin at a purity of 98% or greater.

The peptide that is used in the core tablet is a commercially-available product or a hydrolysis product of food protein manufactured by well-known methods. Examples are peptides obtained by the enzymatic hydrolysis of casein or whey protein (Japanese Patent Publication No. S54-36235 (1979), Japanese Laid-Open Patent Publication No. H7-303455 (1995), Japanese Laid-Open Patent Publication No. H8-112063 (1996) and Japanese Laid-Open Patent Publication No. H8-2286692 (1996). By varying the hydrolysis ratio, peptides that are appropriately modified in terms of molecular weight distribution can be obtained.

The lactoferrin, peptide and lactulose can be used individually or in any combination in the core tablet of the sugar-coated tablet of the present invention. For example, a mixture can be used that is produced by mixing 0.5 part of peptide and 2 parts of lactulose with respect to 1 part of lactoferrin.

In addition, any combination of the aforementioned lactoferrin, peptide and lactulose as well as the aforementioned lactic acid bacteria biomass can be used in the core tablet of the sugar-coated tablet of the present invention.

In addition, other well-known components that are used in drug manufacture can be used as other components in the core tablet of the sugar-coated tablet of the present invention, examples of which include sucrose fatty acid esters, glycerin fatty acid esters and other lubricants, sugars, sweeteners, fragrances, thickeners, and emulsifiers for improving flavor and taste, which may be added in allowed amounts to prepare the raw material for the core tablet. In addition, examples of sugar-coating elements that can be used include well-known shellacs and other water repelling agents, talc, powdered glucose and other dispersants or suspension agents, gum arabic, gelatin and other binders, and colorants, carnauba wax, beeswax and other glossing agents (Hisashi Ichibankase, Kaneto Uekama, and Yuki Odagiri, Eds. "Drug Development [Iyakuhin no Kaihatsu] Vol. 12, Preparation Materials I" p.205, Hirokawa Shoten (1990)).

In the sugar-coated tablet of the present invention, the raw material for the aforementioned core tablet can be milled by means of known milling devices (for example, a rotating pin mill (made by Hosokawa Micron, etc.). Alternatively, the material can be granulated, prior to tabletizing, using a well-known granulator such as an extrusion granulator (for example, the EKUSTURUUDO O MIKKUSU (made by Hosokawa Micron)), or a fluid bed granulator (for example a GURADDO fluidized granulator drier (Okawara Seisakusho)), followed by tabletizing. However, glaze, fragrance and the aforementioned live biomass of the lactic acid bacteria are preferably not granulated.

With the sugar-coated tablet of the present invention, the core tablet is manufactured by using a well known method or device to tabletize the raw material for the core tablet that has been prepared as described above. The device used for tabletizing is a granule compression-type tabletizer, and although any device such as a well-known rotary tabletizer, eccentric tabletizer, etc., can be used, it is preferable to use a rotary tabletizer from the standpoint of productivity on an industrial scale. Specifically, for example, the raw material for the core tablet prepared as described above is supplied to a rotary tabletizer (for example, the HT-PA compact high-speed tabletizer (made by Hata Tekkosho) and the material is compressed between upper and lower molds that provide the shape of the desired tablet, thus forming tablets. The compression force during tabletizing varies depending on the composition of the tablet raw material, the tablet shape, the tabletizing rate and the type of tabletizer, but is normally in the range of 1 to 5 tons. Preliminary compression at a pressure of about 1 ton can also be carried out with the tablet raw material immediately prior to the primary tabletization step.

When the shape of the sugar-coated tablet of the present invention is very unusual, the strength is greatly decreased. In general, however, tabletizing can be carried out using any general tablet shape, such as circular, triangular, square, football-shaped, buckle-shaped, flower-shaped and hat-shaped.

The sugar-coated tablet of the present invention can be manufactured by the well-known pan coating method (for example, using a rotary sugar coating pan (made by Fuji Yakuhin Kikai), etc.) or by a coating method involving a fluidized bed device. Pan coating involves inserting and rotating the core tablets in a pan, while the coating solution is added or sprayed onto the fluid tablet surface by means of a manual operation or automated operation. Dispersant is introduced as necessary, and hot air is directed at the surface of the tablets through a ventilation duct from the front surface of the pan. The solvent is thereby removed and the tablets are dried, which process is repeated any desired number of times to manufacture the sugar-coated tablets (Yoshinobu Nakai, Ed. Drug Development [Iyakuin Kaihatsu] 11, "Unit Processes and Devices for Preparations" [Seizai no Tanisousa to Kikai], p.94, Hirokawa Shoten, 1989). A more detailed description follows.

In manufacturing the sugar-coated tablet of the present invention, a large increase in viscosity at the surface of the tablets is not seen although the tablets that are flowing through the pan assume a wetted state due to the introduction of sugar coating liquid, and each and every tablet exhibits an appropriate fluid condition. As a result, the tablets come into contact with the sugar coating liquid nearly uniformly, so that addition of the sugar coating liquid can be performed by an introduction method or spray method. The shape of the layer and the drying rate at this time depend on the rotation rate of the individual tablets, and thus baffles or floats can be arranged in the pan in order to aid in rotation. The composition ratio of the lactulose and raffinose mixture and the additives (talc, calcium carbonate, calcium phosphate, calcium sulfate, colorant, etc.) in each layer of the sugar coating is 1:0.5 to 2.0 for the sub-coating layer, and 1:0.5–1.2 for the smoothing layer. In the coloring layer, only a mixture of lactulose and raffinose is used, so that the mixing ratio of lactulose and raffinose increases towards the outer layer. Examples of binders that can be added to the sugar coating liquid in order to bind the layers include, in addition to gelatin and gum arabic which have long been used, polyvinyl pyrrolidone or pullulan which is a type of polysaccharide. However, addition of gum arabic is restricted to the subcoating and smoothing layers, where as other binders are used in all of the layers in decreasing concentrations towards the outer layer. Dyes used for coloration are added primarily for coloring.

In finishing the product, a thin finishing layer composed of a mixture of lactulose and raffinose can be formed on the surface to create gloss, and carnauba wax, beeswax and other substances can be used thereon for polishing.

In order also to improve the drying efficiency during coating, a ventilated drying coating device wherein heated air is continually passed through the interior of the rotary mixing bed can be used for manufacturing the sugar-coated tablet of the present invention (for example, a rotary type coater (made by Furointo Sangyo)). With this device, the cylindrical pan has a double-layer structure, with punch holes provided on the inner side. Because the pan causes dry air to flow in the spaces between the tablets that constitute a rotating mixing bed, the drying efficiency is increased at about 1.5–2 times with respect to ordinary pans. Also, a reverse-format device wherein the dry air is made to flow from the outside rather than the inside can also be used for manufacturing the sugar-coated tablet of the present invention.

The sugar-coated tablet of the present invention manufactured as described above makes it possible to uniformly apply a sugar coating base onto a core tablet by means of mixing prescribed amounts of raffinose, in spite of the fact that it is difficult to coat lactulose alone on core tablets. A product is thus obtained that has good external appearance as well as excellent physiological effects and taste (mouthfeel) not attainable with conventional products.

A fuller understanding of the present invention is provided through the following test examples.

TEST EXAMPLE 1

This test was carried out in order to compare the effects of raffinose with that of other sugars such as the oligosaccharides lactosucrose and paratinose, and the sugar alcohols maltitol and erythritol, in production of the sugar-coated tablet of the present invention when used with lactulose.

1) Sample Preparation

Lactulose powder (made by Morinaga Milk Industry Co., Ltd.) was blended at a ratio of 1 part with respect to 1 part of cell powder (live cells counted: $100 \times 10^8$/g, Morinaga Milk Industry Co., Ltd.) of Bifidobacterium longum M-8201 (Bikouken accession no. 6548, at National Institute of Bioscience and Human Technology). To 97 parts of the resulting mixture was added 3 parts of glycerin fatty acid ester (made by Riken Vitamin) as glaze, and the substances were mixed until uniform to prepare the raw material for the core tablet. The raw material for the core tablet was tabletized at a tabletizing pressure of 1 ton using a rotary table tabletizer equipped with a 5 mm diameter round tabletizing pestle to prepare 10,000 round tablets of diameter 5 mm and weight 0.2 g.

A mixture produced by blending 3 parts of raffinose powder (made by Nihon Tensai Seitou) with 1 part of lactulose powder (made by Morinaga Milk Industry Co., Ltd.) used as sugar coating base was dissolved in water at 70° C. to prepare a 50% aqueous solution (Sample 1).

Separately, mixtures produced by blending 3 parts each of lactosucrose powder (made by Ensuikou Seitou; sample 2), paratinose powder (made by Mitsui Seitou; sample 3), erythritol powder (made by Nikken Chemicals Co., Ltd.; sample 4) and maltitol powder (made by Towa Kasei Kogyo; sample 5) with 1 part of lactulose powder (made by Morinaga Milk Industry Co., Ltd.) used as sugar coating bases were dissolved in water at 70° C. to prepare each of 50% aqueous solution.

Subsequently, 1 kg (about 5000 tablets) of the aforementioned core tablet was introduced into a pan sugar coater (Fuji Seihin Kikai; 300ϕ), and was subjected to sugar coating treatment with the sugar coating base of sample 1 above distributed in small amounts, under conditions of a pan rotation rate of 30 rpm, a ventilation air temperature of 50° C., and a ventilation air quantity of 0.1 m$^3$ to prepare sugar-coated tablets of about 0.4 g/tablet. Sugar-coated tablets were also prepared for samples 2 to 5 above using the same method.

2) Test Method 100 tablets were taken at random from each of the resulting samples, and comparative testing was carried out in regard to production condition during pan-coating manufacture, external appearance (coating uniformity), and taste (mouthfeel).
i) Production Condition During Pan-coating Manufacture During manufacture, the production condition was evaluated by observing the state of movement of the sugar-coated tablets in the rotating pan, and periodically stopping the pan rotation to check for sticking or adhesion between the sugar-coated tablets by touching with the hand.
ii) External Appearance (Coating Uniformity)

The condition of the front and back surfaces of 100 of the sugar-coated tablets taken from each of the samples was visually observed and the condition was evaluated in four levels, with "good" denoting equivalent condition compared with commercially-available sugar-coated tablets, followed by "fairly good", "somewhat poor" and "poor".
iii) Taste (Mouthfeel)

2 to 3 tablets as appropriate from among the 100 tablets were placed in the mouth to investigate the taste when ingested. This procedure was repeated 4–5 times, and the taste (mouthfeel) was evaluated in four levels: "good", "fairly good", "somewhat poor" and "poor".

3) Test Results

The results of this test are shown in Table 1. As is clear from Table 1, with sugar-coated tablets formed by mixing lactosucrose or paratinose with lactulose as sugar coating base (sample 2 and sample 3), the viscosity of a mixed aqueous solution of the samples was high, and the tablets adhered in clumps during manufacture, and the coating on the sugar-coated tablets was uniform, but the taste (mouthfeel) thereof was poor. In addition, with sugar-coated tablets produced by mixing erythritol (sample 4), the viscosity of a mixed aqueous solution of the sample was comparatively low relative to the other samples, but adhesion between tablets occurred during manufacture. With the sugar-coated tablets produced by mixing maltitol (sample 5), the viscosity of a mixed aqueous solution of the sample was high, and the tablets adhered together during manufacture to form clumps, and the coating of the sugar-coated tablets was not uniform, and the taste (mouthfeel) thereof was also poor. In contrast, with the sugar-coated tablets in which raffinose was mixed with the lactulose (sample 1), the viscosity of a mixed aqueous solution of the sample was low, no adhesion between tablets occurred during manufacture, coating of the sugar-coated tablets was uniform, and the taste (mouthfeel) thereof was good.

TABLE 1

| Sample | Viscosity of 50% aqueous solution of various sugars (mPa · s) | Pan coating manufacture condition | Condition of sugar-coated tablets | |
|---|---|---|---|---|
| | | | Coating uniformity | Mouthfeel |
| Sample 1 | 13.2 | Almost no tablet adhesion | Good | Good |
| Sample 2 | 20.9 | Tablets form clumps | Poor | Poor |
| Sample 3 | 16.5 | Adhesion between tablets | Poor | Poor |
| Sample 4 | 13.7 | Some adhesion of tablets | Somewhat poor | Somewhat poor |
| Sample 5 | 18.0 | Tablets form clumps | Poor | Poor |

Note: Viscosity represents value at 25° C..

TEST EXAMPLE 2

This test was carried out in order to investigate mixing ratios between lactulose and raffinose used in the tablet preparations.

1) Preparation of Samples

Round sugar-coated tablets of about 0.4 g per tablet were prepared using the same method as in Test Example 1, except that 0 to 19 parts of raffinose powder (made by Nihon Tensai Seitou) as indicated in Table 2 was mixed with respect to 1 part of lactulose powder (made by Morinaga Milk Industry Co., Ltd.) to produce mixtures to be used as sugar coating bases for coating core tablets, and the mixtures were then dissolved in water at 70° C. to produce 50% aqueous solutions.

2) Test Method

Testings for external appearance and taste (mouthfeel) of the samples were carried out using the same methods as in Test Example 1 above.

3) Test Results

The results of the tests are shown in Table 2. As is clear from Table 2, along with an increase in raffinose mixing ratio occurred a trend towards decreased viscosity of the mixed aqueous solution, and decrease adhesion between tablets during manufacture thereof. Coating of the resulting sugar-coated tablets was uniform, and the taste (mouthfeel) of the same was also good. Consequently, it was clear that an aqueous solution of a mixture comprising 1 part raffinose and 1 part lactulose is the lower limit at which it is possible to maintain good sugar coating manufacture conditions and good sugar-coated tablet condition in the pan coating method.

Moreover, as is clear from Table 2, an aqueous solution of a mixture composed of 10 parts raffinose and 1 part lactulose is the threshold at which generation of raffinose crystal powder occurs during sugar coating manufacture by the pan coating method. It was thus confirmed that this is the preferred upper limit for the lactulose and raffinose mixture used for the sugar coating base for the sugar-coated tablet of the present invention. However, this upper limit defines a preferred range, and does not mean that sugar-coated tablets cannot be manufactured in spite of the generation of raffinose crystal powder.

TABLE 2

| Lactulose and raffinose mixing ratio | | 50% aqueous solution | Pan | Sugar-coated tablet condition | |
|---|---|---|---|---|---|
| Lu (%) | La (%) | viscosity (mPa · s) | coating manufacture condition | Coating uniformity | Mouthfeel |
| 50 | 0 | 20.9 | Tablets formed clumps | Poor | Poor |
| 40 | 10 | 18.0 | Tablets adhered to each other | Poor | Poor |
| 30 | 20 | 16.3 | Adhesion during drying poor | Somewhat poor | Somewhat poor |
| 25 | 25 | 14.7 | Slight adhesion | Fairly good | Fairly good |
| 20 | 30 | 13.2 | Almost no adhesion | Good | Good |
| 10 | 40 | 11.4 | No adhesion during drying | Good | Good |
| 5 | 45 | 10.6 | No adhesion during drying | Good | Good |
| 4.5 | 45.5 | 10.5 | Slight raffinose crystal generation | Fairly good | Fairly good |
| 4 | 46 | 10.4 | Fair amount of raffinose crystal generation | Fairly good | Fairly good |
| 2.5 | 47.5 | 10.2 | Large amount of raffinose crystal generation | Fairly good | Fairly good |

Note: Lu and La denote lactulose and raffinose. For other notes, refer to Table 1.

REFERENCE EXAMPLE 1

Bifidobacterium longum M-8201 (Bikouken accession no. 6548, at National Institute of Bioscience and Human Technology) was cultured for 10 generations using ABCM medium (made by Eiken Kagaku) containing glucose, and then was inoculated into 50 L of synthetic medium composed of glucose, yeast extract, peptone and phosphate to culture the same for 14 h at 37° C. The resulting culture was then collected by centrifugal separation, and 1 L of the resulting bacterial solution was dispersed in 500 mL of dispersion medium produced by dissolving 100 g of glutamic acid (made by Wako Pure Chemical) and 50 of sucrose in water, and then was freeze-dried to obtain the microbial cells powder.

To 275 g of the resulting powdered cells was added 2 kg of lactose (made by Wako Pure Chemical) and 2.5 kg of dry corn starch (made by Matsutani Kagaku Koyo), and the materials were mixed and dispersed to obtain 4.7 kg of powdered cells of Bifidobacterium longum (live cells counted: $110 \times 10^8$/g).

REFERENCE EXAMPLE 2

4.0 kg of powdered cells of Streptococcus faecalis (live cells counted: $230 \times 10^8$/g) were obtained by the same method as in Reference Example 1, except that Streptococcus faecalis ATCC-19433 was used.

REFERENCE EXAMPLE 3

4.5 kg of powdered cells of Lactobacillus acidophilus (live cells counted: $340 \times 10^8$/g) were obtained by the same method as in Reference Example 1, except that Lactobacillus acidophilus ATCC-4356 was used.

REFERENCE EXAMPLE 4

3.5 kg of powdered cells of Leuconostoc cremoris (live cells counted: $50 \times 10^8$/g) were obtained by the same method as in Reference Example 1, except that Leuconostoc cremoris ATCC-19254 was used.

BEST MODE FOR CARRYING OUT THE INVENTION

A fuller understanding of the present invention is provided below through examples, and these examples, however, are not limiting of the invention.

EXAMPLE 1

50 kg powdered live cells of Bifidobacterium longum manufactured by the same method as in Reference Example 1, 25 kg of lactulose (made by Morinaga Milk Industry Co., Ltd.), 21.6 kg of maltitol (made by Towa Kasei Kogyo), 3 kg of glycerin fatty acid ester (made by Riken Vitamin) and 0.4 kg of yogurt flavor (made by Nagasegawa Koryou) were mixed until uniform, and were tabletized at a tabletizing pressure of 1 ton using a rotary table tabletizer (made by Hata Tekkosho) to produce 490,000 triangular core tablets at about 0.2 g per tablet.

The resulting core tablets were introduced into a pan sugar coater (1500φ, Fuji Yakuhin Kikai), and were subjected to sugar coating treatment with a 50% aqueous solution of a mixture composed of 1.5 parts raffinose and 1 part lactulose introduced as sugar coating base into a pan, under conditions of a pan rotation rate of 6 rpm, a ventilated air temperature of 60° C., a ventilated air amount of 10 m³/min and an exhaust air amount of 1/min to obtain approximately 0.4 g triangular sugar-coated tablets with no adhesion between tablets.

The resulting sugar-coated tablets were tested by the same method as in Test Example 1, and the results indicated a uniform coating, good taste (mouthfeel) and a live cells count of $25 \times 10^8$/g.

EXAMPLE 2

488,000 triangular sugar-coated tablets of about 0.2 g per tablet were obtained by the same method as in Example 1, except that 25 kg of each of the lactic acid bacteria cells powders manufactured by the same methods as in Reference Example 2 and Reference Example 3, 20 kg of peptide (made by Morinaga Milk Industry Co., Ltd.; CU2500), 10 kg of lactulose (made by Morinaga Milk Industry Co., Ltd.), 17 kg of maltitol (made by Towa Kasei Kogyo) and 3 kg of sugar ester (made by Dai-ichi Kogyo Seiyaku) were mixed until uniform, and were tabletized at a tabletizing pressure of 1.5 ton with a rotating table tabletizer (made by Hata Tekkosho), using a 50% aqueous solution of a mixture of 1 part lactulose and 1 part raffinose as the sugar coating base.

The resulting sugar-coated tablets were tested by the same method as in Test Example 1, and the results indicated a uniform coating, good taste (mouthfeel) and a live cells count of $70 \times 10^8$/g.

EXAMPLE 3

492,000 triangular sugar-coated tablets of about 0.2 g per tablet were obtained by the same method as in Example 1, except that 25 kg of each of the lactic acid bacteria cells powders manufactured by the same methods as in Reference Example 1 and Reference Example 4, 10 kg of lactoferrin (made by Morinaga Milk Industry Co., Ltd.), 10 kg of peptide (made by Morinaga Milk Industry Co., Ltd.; CU2500), 27 kg of maltitol (made by Towa Kasei Kogyo) and 3 kg of glycerin fatty acid ester (made by Riken Vitamin) were mixed until uniform, and were tabletized at a tabletizing pressure of 2 ton with a rotating table tabletizer (made by Hata Tekkosho), using a 50% aqueous solution of a mixture of 1 part lactulose and 4 parts raffinose as the sugar coating base.

The resulting sugar-coated tablets were tested by the same method as in Test Example 1, and the results indicated a uniform coating, good taste (mouthfeel) and a live cells count of $20 \times 10^8$/g.

EXAMPLE 4

491,000 triangular sugar-coated tablets of about 0.2 g per tablet were obtained by the same method as in Example 1, except that 80 kg of lactoferrin (made by Morinaga Milk Industry Co., Ltd.), 17 kg of maltitol (made by Towa Kasei Kogyo) and 3 kg of sugar ester (made by Dai-ichi Kogyo Seiyaku) were mixed until uniform, and were tabletized with a rotating table tabletizer (made by Hata Tekkosho) at a tabletizing pressure of 1 ton, using a 50% aqueous solution of a mixture of 1 part lactulose and 10 parts raffinose as the sugar coating base.

The resulting sugar-coated tablets were tested by the same method as in Test Example 1, and the results indicated a uniform coating and good sensation (feel).

EXAMPLE 5

495,000 triangular sugar-coated tablets of about 0.2 g per tablet were obtained by the same method as in Example 1, except that 80 kg of peptide (made by Morinaga Milk Industry Co., Ltd.), 17 kg of maltitol (made by Towa Kasei Kogyo) and 3 kg of glycerin fatty acid ester (made by Riken Vitamin) were mixed until uniform, and were tabletized with a rotating table tabletizer (made by Hata Tekkosho) at a tabletizing pressure of 1.5 ton, using a 50% aqueous solution of a mixture of 1 part lactulose and 8 parts raffinose as the sugar coating base.

The resulting sugar-coated tablets were tested by the same method as in Test Example 1, and the results indicated a uniform coating and good taste (mouthfeel).

EXAMPLE 6

497,000 triangular sugar-coated tablets of about 0.2 g per tablet were obtained by the same method as in Example 1, except that 97 kg of lactulose (made by Morinaga Milk Industry Co., Ltd.) and 3 kg of glycerin fatty acid ester (made by Riken Vitamin) were mixed until uniform, and were tabletized with a rotating table tabletizer (made by Hata Tekkosho) at a tabletizing pressure of 1 ton, using a 50% aqueous solution of a mixture of 1 part lactulose and 1.2 parts raffinose as the sugar coating base.

The resulting sugar-coated tablets were tested by the same method as in Test Example 1, and the results indicated a uniform coating and good taste (mouthfeel).

INDUSTRIAL APPLICABILITY

As described above, the present invention is a sugar-coated tablet produced by coating a core tablet with a sugar coating base containing, as effective component, a mixture of lactulose and raffinose. The present invention exhibits the following effects:

1) a sugar coated tablet is provided, which employs ilactulose and raffinose having various physiological effects, without using a conventional sugar coating base;
2) a sugar-coated tablet is provided, which has equivalent product quality to that of sugar-coated tablets produced using sucrose and has anticariogenic properties; and
3) a sugar-coated tablet is provided, which does not stick to the oral cavity when taken, has no unpleasant texture when ingested, and has good taste (mouthfeel) and excellent flavor.

What is claimed is:

1. A sugar-coated tablet which comprises:
   a core tablet; and
   a sugar coating base;
   wherein the core tablet is coated with said sugar coating base and said sugar coating base comprises a mixture of 1 part by weight of lactulose and at least 1 part by weight of raffinose.

2. The sugar-coated tablet according to claim 1, wherein the core tablet comprises, one or both of (a) and (b) below:
   (a) a cell powder of one or more microorganisms selected from the group consisting of a microorganism of the genus Bifidobacterium, a microorganism of the genus Lactobacillus, a microorganism of the genus Streptococcus, a microorganism of the genus Pediococcus and a microorganism of the genus Leuconostoc, and
   (b) one or more compounds selected from the group consisting of lactoferrin, a peptide, lactulose and a mixture thereof.

3. The sugar coated tablet according to claim 1, wherein said sugar coating base comprises 1.5 to 10 parts by weight of raffinose.

4. The sugar coated tablet according to claim 1, wherein said core tablet comprises a lactic acid bacteria biomass powder.

5. The sugar coated tablet according to claim 4, wherein said lactic acid bacteria biomass powder is alive or dead.

6. A method for intestinal regulation, comprising:
   administering the sugar coated tablet according to claim 4, to a subject in need thereof.

7. The sugar coated tablet according to claim 2, wherein said core tablet comprises 0.5 parts by weight of peptide, 2 parts by weight of lactulose based on 1 part by weight of lactoferrin.

8. The sugar coated tablet according to claim 2, wherein said core tablet further comprises a sucrose fatty acid ester, a glycerin fatty acid ester, a sugar, a sweetener, a fragrance, a thickener, an emulsifier.

9. The method according to claim 6, wherein said core tablet comprises, one or both of (a) and (b) below:

(a) a cell powder of one or more microorganisms selected from the group consisting of a microorganism of the genus Bifidobacterium, a microorganism of the genus Lactobacillus, a microorganism of the genus Streptococcus, a microorganism of the genus Pediococcus and a microorganism of the genus Leuconostoc, and (b) one or more compounds selected from the group consisting of lactoferrin, a peptide, lactulose and a mixture thereof.

10. The method according to claim 6, wherein said sugar coating base comprises 1.5 to 10 parts by weight of raffinose.

11. The method according to claim 6, wherein said core tablet comprises 0.5 parts by weight of peptide, 2 parts by weight of lactulose based on 1 part by weight of lactoferrin.

12. The method according to claim 6, wherein said core tablet further comprises a sucrose fatty acid ester, a glycerin fatty acid ester, a sugar, a sweetener, a fragrance, a thickener, an emulsifier.

* * * * *